United States Patent [19]

Barenholz et al.

[11] Patent Number: 5,043,166

[45] Date of Patent: Aug. 27, 1991

[54] LIPOSOME/ANTHRAQUINONE DRUG COMPOSITION AND METHOD

[75] Inventors: Yechezkel Barenholz, Jerusalem, Israel; Alberto Gabizon, San Francisco, Calif.

[73] Assignees: Hadasit Medical Research, Inc.; Yissum Research and Development Company et al., both of Jerusalem, Israel

[21] Appl. No.: 436,469

[22] Filed: Nov. 14, 1989

Related U.S. Application Data

[63] Continuation of Ser. No. 256,844, Oct. 12, 1988, Pat. No. 4,898,735, Continuation-in-part of Ser. No. 806,084, Dec. 6, 1986, Pat. No. 4,797,285.

[51] Int. Cl.$^5$ ............................................. A61K 37/22
[52] U.S. Cl. ...................................................... 424/450
[58] Field of Search .................................. 424/450, 417

[56] References Cited

U.S. PATENT DOCUMENTS

| | | | |
|---|---|---|---|
| 3,993,754 | 11/1976 | Rahman et al. | 514/12 |
| 4,310,506 | 1/1982 | Baldeschwieler et al. | 424/1.1 |
| 4,397,867 | 9/1983 | Blake | 514/575 |
| 4,460,560 | 7/1984 | Tokes et al. | 424/1.1 |
| 4,610,868 | 9/1986 | Fountain et al. | 424/1.1 |
| 4,797,285 | 1/1989 | Barenholz et al. | 424/417 |
| 4,898,735 | 2/1990 | Barenholz et al. | 424/450 |

FOREIGN PATENT DOCUMENTS

0084898 8/1983 European Pat. Off. .

OTHER PUBLICATIONS

6-General Biochem, vol. 98, p. 67309 (1983), "98:67308y", Adriamycin-Dependent Damage to Deoxyribose: A Reaction Involving Iron, Hydroxyl and Semiquinone Free Radicals.
Chemical Abstracts, vol. 104 (1986), p. 34, "104:141870m", Prevention of Doxorubicin-Induced Killing of MCF-7 Human Breast Cancer Cells by Oxygen Radial Scavengers and Iron Chelating Agents, Koroshow, James H. (Dep. Med. Oncol.).
1-Pharmacology, vol. 100 (1984), p. 17333, "100:17330p", Free Radical Metabolism of VP-16 and Inhibition of Anthracyline-Induced Lipid Peroxidation, Sinha, Birandra K.; Trush, Michael A.; Kalyanaraman, Balaraman (Lab. Med. Chem. Pharmacol.), 1983.
63-Pharmaceuticals, vol. 94 (1981), p. 197507, "94:197501j", Liposome-Encapsulated Desferrioxamine in Experimental Iron Overload, Lau, E. H.; Cerny, E. A.; Rahman, Y. E.
Chemical Abstracts, 95:12709n (1981), "Application of Liposomes to Metal Chelation Therapy", Rahman Y. E., et al.

Primary Examiner—Frederick E. Waddell
Assistant Examiner—Kevin Weddington
Attorney, Agent, or Firm—Peter J. Dehlinger

[57] ABSTRACT

A drug/liposome composition comprising an aqueous suspension of liposomes and, entrapped in the lipid bilayer region of the liposomes, an anthraquinone drug containing quinone and hydroquinone functionalities on adjacent anthracene rings. An iron-specific trihydroxamic chelating agent contained in the bulk aqueous phase of the suspension and a lipophilic free-radical scavenger contained in the bilayer region of the liposome cooperate to reduce chemical modification of both drug and lipid components of the composition. A preferred composition containing doxorubicin and alpha-tocopherol entrapped in the liposomes, and ferrioxamine in the aqueous suspension phase is effective in treating human neoplasms, with significantly reduced side effects over those produced by free-drug administration.

9 Claims, 6 Drawing Sheets

LIPOSOME/ANTHRAQUINONE DRUG COMPOSITION AND METHOD

This application is a continuation of U.S. application Ser. No. 07/256,844, filed Oct. 12, 1988, issued 6 Feb. 1990 as U.S. Pat. No. 4,898,735, which is a continuation-in-part of U.S. Ser. No. 06/806,084, filed Dec. 6, 1986 now U.S. Pat. No. 4,797,285, issued 10 Jan. 1989.

1. FIELD OF THE INVENTION

The present invention relates to an improved liposome/anthraquinone therapeutic composition having reduced lipid oxidation and free-radical damage, and to methods for preparing and using the composition.

2. REFERENCES

Aubel-Sadron, G., et al, Biochemie, 66:333 (1984).
Augustin, M. A., J Am Oil Chem, 60:105 (1983).
Forssen, E. A., et al, Proc Nat Acad Sci, USA, 78(3) 1873 (1981).
Gabizon, A., et al, Cancer Res, 42:4734 (1982).
Gabizon, A., et al, Cancer Res, 43:4730 (1983).
Gabizon, A., et l, Brit J Cancer, 51:681 (1985).
Goormaghtigh, E., et al, Res Commun Chem Path and Pharm, 42(1):149 (1983).
Goormaghtigh, E., et al, Biochem Biophys Acta, 779:271 (1984).
Gutteridge, J.M.C. Biochem Pharm, 33(11):1725 (1984a).
Gutteridge, J.M.C., FEBS, 172(2):245.
Juliano, R. L., et al, Biochem Pharmacol, 27:21 (1978).
Klein, R. A., Biochem Biophys Acta, 210:486 (1970).
Mayhew, E., et al, Cancer Treat Repts, 63 (11–12):1923 (1979).
Myers, C. E., et al, Cancer Treat Repts, 60(7):961 (1976).
Olson, F., et al, Eur J Clin Oncol, 18(2):167 (1982).
Poznansky, M. L., et al, Pharm Revs 36(4):277 (1984).
Rahman, A., et al, Cancer Res, 40:1532 (1980).
Samuni, A., et al, Cancer Res, in press.
Sikic, B. I., et al, Science, 228:1544 (1985).
Sonneveld, P., Cancer Treat Repts, 62(7):1033 (1978).
Stuart-Harris, R. C., et al, Biochem Pharmacol, 12:1 (1984).
Sunamoto, J., et al, Biochem Biophys Acta, 833:144 (1985).
Szoka, F., et al, Ann Rev Biophys Bioeng, 9:467 (1980).
Tomasz, M., Chem-Biol Interact, 13:89 (1976).
Wang, Y. M., et al, Cancer Res, 40:1022 (1980).
Young, R. C., et al, N Eng J Med, 305:139 (1981).

3. BACKGROUND OF THE INVENTION

Liposome delivery systems have been proposed for a variety of drugs, particularly those which are administered parenterally. Liposomes have the potential of providing a controlled "depot" release of the administered drug over an extended time period, and of reducing toxic side effects of the drug, by limiting the concentration of free drug in the bloodstream. Liposomes can also alter the tissue distribution and uptake of drugs, and the altered tissue distribution, combined with other advantages just mentioned, can significantly increase the therapeutic effectiveness of the drug. Liposome/drug compositions can also increase the convenience of therapy by allowing higher drug dosage and less frequent drug administration. Liposome drug delivery systems are reviewed generally in Poznansky et al.

One group of drugs whose use in liposome delivery systems has been widely studied is the class of anthracene quinones, including, particularly, the anthracycline glycoside antibiotics, exemplified by the antitumor drug doxorubicin or "Adriamycin", doxorubicinol, daunorubicin, and daunorubicinol, and their cyanomorpholinyl derivatives. Doxorubicin (DXR) is a potent chemotherapeutic agent effective against a broad spectrum of neoplasms (Aubel-Sadron et al and Young). However, use of the drug in soluble form is limited by serious side effects. Its acute toxicity includes malaise, nausea, vomiting myelosuppression, and severe alopecia. In addition, cumulative and irreversible cardiac damage occurs with repeated administration, which seriously limits the use of the drug in protracted treatment (Young). When administered in liposome form, the drug retains its therapeutic effectiveness against animal tumors, but is significantly less toxic, as judged by reduced mortality (Forssen, Gabizon 1985). The drug-protective effect of liposomes is due, at least in part, to a marked alteration in tissue disposition and drug-release rate of the injected drug (Gabizon 1982; Gabizon 1983; Juliano).

The cardiomyopathy observed in doxorubicin treatment is similar to the cardiac muscle lesions seen in experimental animals under conditions of alpha-tocopherol ($\alpha$-T) deficiency (Tomasz), suggesting that the drug-induced lesions are caused by increased free-radical reactions involving membrane lipids. DXR and other anthraquinones, which have the general structure shown in FIG. 1, contain both quinone and hydroquinone groups, and thus might be expected to promote peroxidation reactions involving electron transfer to or from the quinones or hydroquinones. In addition, binding of the drug to lipids through the anthracene moiety would be expected to facilitate lipid involvement in peroxidations reactions. It is known, for example, that DXR binds tightly to cardiolipin, a major lipid component in mitochondria, and enzyme-catalyzed electron transport results in formation of covalent linkages between the drug and lipid (Goormaghtigh).

The free radical mechanism of cardiac toxicity proposed for DXR suggests that a lipophilic free-radical quencher such as vitamin E would be effective in reducing drug toxicity and this, in fact has been found (Myers; Wang; Sonneveld). The referenced studies have shown that vitamin E is effective in reducing cardiotoxicity when administered prior to or concurrent with DXR administration. More recent studies have shown that a liposome drug system with coentrapped DXR and vitamin E is less toxic in animals, and produces less cardiomyopathy, than either vitamin E/DXR or liposome/DXR combinations alone (Olson). The reduced toxicity of liposomes with coentrapped DXR and vitamin E apparently results from a combination of the altered drug distribution and/or lower free drug levels—due to liposomal entrapment of the drug—and from reduced free-radical damage—due to the free-radical quenching activity of vitamin E.

Despite the reduced toxicity of a liposome/DXR/vitamin E formulation, it has been found, in studies conducted in support of the present invention, that the drug and lipids in such formulation can undergo substantial chemical modification, even under anoxic during storage conditions. Such damage increases the toxicity of the drug formulation and appears to compromise the therapeutic action of the drug.

4. SUMMARY OF THE INVENTION

The present invention includes a liposome/anthraquinone composition having anti-oxidant properties designed to reduce lipid oxidation and free radical damage to both the lipid and drug components of the composition.

According to the invention, it has been discovered that drug and lipid damage related to oxidative and free-radical mechanisms is substantially reduced by including in the liposome formulation, a lipophilic free-radical scavenger, such as $\alpha$-T, and a water-soluble trihydroxamic acid chelating agent, such as ferrioxamine, having a high and selective binding affinity for ferric iron. The extent of protection against lipid-peroxidation and free-radical damage is much greater than that afforded by free-radical quenchers alone or by chelating agents, such as ethylenediamine tetraacetic acid (EDTA), which have been used heretofore. The chelating agent is present in a molar excess of the ferric iron in the suspension.

One preferred liposome composition contains DXR (or a pharmacologically acceptable analog, derivative, or salt thereof) at a molar ratio of at least about 2.5 mole percent in liposomes composed 20-50 mole percent cholesterol, 10-40 mole percent negatively charged phospholipid, such as phosphatidylglycerol (PG), phosphatidylserine (PS) or phosphatidylinositol (PI), and phosphatidylcholine (PC). The liposomes are predominantly in the size range of 0.05 to 0.5 microns, and the amount of free drug in the suspension—that is, drug not associated with liposomes—is preferably less than about 15% of the total drug in the suspension. Ferrioxamine is contained in the suspension at about 50 $\mu$M, and $\alpha$-T in the liposomes, at a concentration of at least about 0.2 mole percent.

Also included in the invention is a method for treating human neoplasms with a DXR/liposome composition formed as above. Clinical trials on human cancer patients in the frame of a Phase I study indicate significant reduction of many side effects such as discomfort (malaise), headaches, nausea, vomiting, local pain at the site of injection, and alopecia, frequently associated with treatment by free DXR. In addition, anti-tumor activity has been shown on hepatocellular carcinoma.

It is one general object of the invention to provide a liposome composition containing an entrapped anthraquinone drug in which in vitro peroxidative damage to the lipid and drug components of the composition is substantially reduced.

Another object of the invention is to provide a general method for reducing, in a liposome/anthraquinone composition, lipid and drug toxicity which are related to oxidation and free-radical reactions.

A specific object is to provide such a composition for treatment of human neoplasm, wherein the drug is DXR or a pharmacologically accepted analogue, derivative, or salt thereof.

A related object of the invention is to provide a method of treating human neoplasms, and, particularly, primary and metastatic liver tumors, hematopoietic proliferative disorders, and leukemias with liposome-entrapped DXR with significant amelioration of normal drug side effects.

These and other objects and features of the invention will become more fully apparent when the following detailed description of the invention is read in conjunction with the accompanying drawings.

DETAILED DESCRIPTION OF THE INVENTION

I. Preparing the Liposome/Drug Composition

A. The Anthraquinone Drug

The anthraquinone drug used in preparing the composition of the invention is an anti-neoplastic anthraquinone drug having an anthracene ring structure and quinone, semi-quinone, or hydroquinone functionalities carried on the ring structure. More precisely, and as the term is defined herein, anthraquinone drugs include those anthraquinone structures having one quinone and hydroquinone group on adjacent rings of the anthracene ring structure. Anti-neoplastic anthraquinones having these features can be classed into three groups which are illustrated in FIGS. 1A-1C.

Figure 1A:
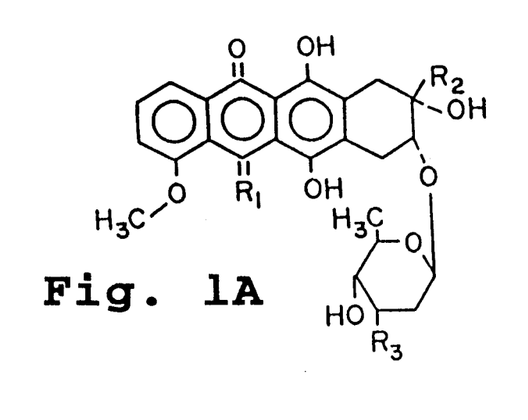
FIGS. 1A-1C show the general structures of class I and II anthracycline aminoglycosides (1A and 1B, respectively), and mitoxanthrone (1C)
Figure 1B:
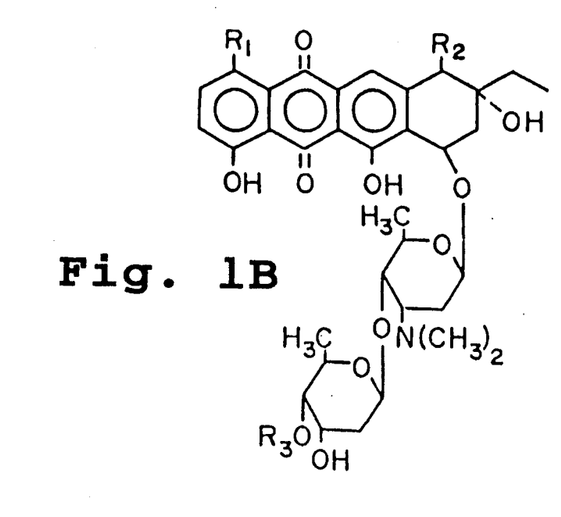
Figure 1C:
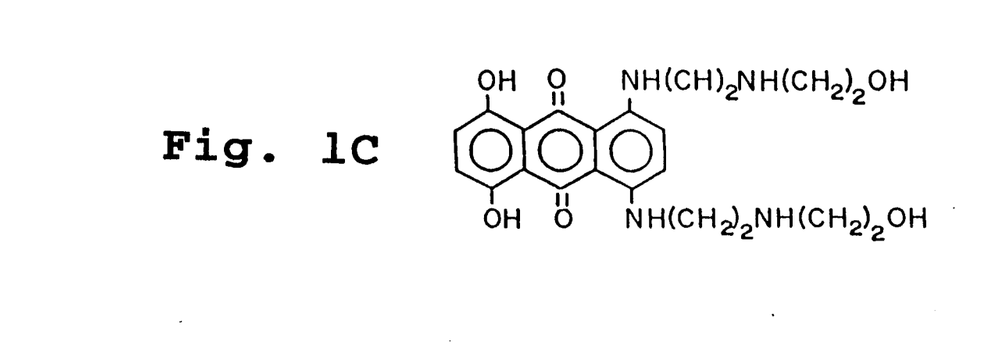

The first group is the class I anthracene glycosides which are illustrated in FIG. 1A. Included in this group are a number of clinically important anti-neoplastic drugs, such as doxorubicin (DXR, commonly known as Adriamycin), daunomycin, carcinomycin, N-acetyladriamycin, N-acetyldaunomycin, rubidazone, and 5-imidodaunomycin. Table I below gives the structural variations of the these several class I drugs, in terms of the R1, R2, and R3 groups in FIG. 1A. More recently, a cyanomorpholino derivative of DXR has been reported (Sikic). Drugs in this class are known to have anti-neoplastic effects against a variety of cancers, including acute leukemias, breast cancer, Hodgkin disease, non-Hodgkin lymphomas, and sarcomas. The primary mechanism of the drugs appears to be intercalation into DNA and DNA damage (Young, Goormaghtigh 1984), although membrane binding (Goormaghtigh 1984) and enzyme catalyzed free-radical formation (Aubel-Sadron) have also been suggested as possible contributing mechanisms of drug action.

TABLE I

| | $R_1$ | $R_2$ | $R_3$ |
|---|---|---|---|
| Adriamycin | =O | —CO—CH$_2$OH | —NH$_2$ |

TABLE I-continued

| | R₁ | R₂ | R₃ |
|---|---|---|---|
| Daunomycin | =O | —CO—CH₃ | —NH₂ |
| N-Acetyladriamycin | =O | —CO—CH₂OH | —NH—CO—CH₃ |
| N-Acetyl-daunomycin | =O | —CO—CH₃ | —NH—CO—CH₃ |
| Rubidazone | =O | C—N—N-H—C—CH₃O | —NH₂ |
| 5-Imidodaunomycin | =NH | —CO—CH₃ | —NH₂ |

The second group includes the class II anthracene glycosides, which are distinguished from the class I compounds by more complex (multimeric) aminoglycoside residues, as seen in FIG. 1B. These compounds share the same general therapeutic and toxicity properties of their class I counterparts. Representative class II anthracene aminoglycosides are listed in Table II, with reference to the R1, R2, and R3 groups shown in FIG. 1B.

TABLE II

| Anthracycline | R₁ | R₂ | R₃ |
|---|---|---|---|
| Musettamycin | OH | COOCH₃ | H |
| Rudolfomycin | OH | COOCH₃ | Rednosamine |
| Aclacinomycin | H | COOCH₃ | Cinerulose |
| Marcellomycin | OH | COOCH₃ | 2-Deoxyfucose |
| Descarbomethoxy-marcellomycin | OH | H | 2-Deoxyfucose |
| Descarbomethoxy-rudolfomycin | OH | H | Rednosamine |

The third group of anthraquinones includes those which have the general ring structure shown in FIG. 1A, i.e., with quinone and hydroquinone groups on adjacent anthracene rings, but which lack the glycoside groups characteristic of the anthracycline antibiotics. One important drug in this group is mitoxanthrone, an anti-neoplastic drug which is reported to be effective against a variety of cancers, including breast cancer, but which may have reduced side effects, including cardiotoxicity, when compared with free DXR (Stuart-Harris).

Figure 2:
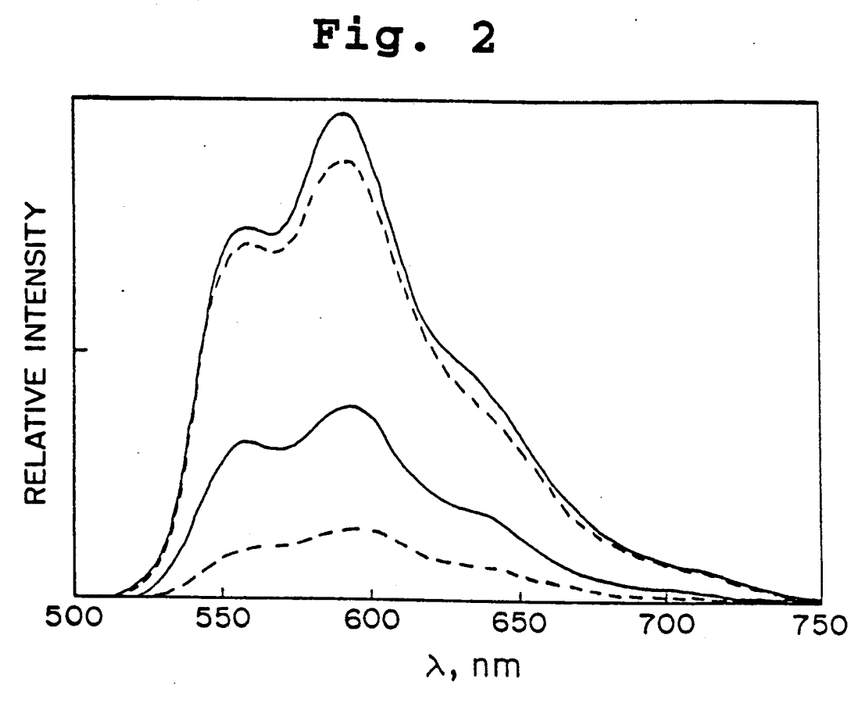
FIG. 2 shows the fluorescent emission spectra of DXR in soluble (upper dashed line) and liposome-bound (upper solid line) form, and a DXR-Fe (III) complex in soluble (lower dashed line) and freshly prepared liposome-bound (lower solid line) form.

Studies on the binding of ferric iron to DXR which have been carried out in collaboration with one of the inventors indicate that the anthraquinone drugs, and particularly the anthracyclic aminoglycosides, form stable metal complexes with ferric iron (Samuni). The studies examined the binding of DXR to ferric iron, both in the presence and absence of small unilamellar vesicles (SUVs) formed from the saturated phospholipid dimyristylphosphatidylcholine (DMPC). With reference to FIG. 2, the fluorescent emission spectrum of DXR at 480 nm excitation wavelength (upper dashed line) shows peaks at about 590 and 560 nm, and this spectrum is changed very little when the drug is associated with SUVs (upper solid line). When DXR is complexed with ferric iron in the presence of ADP, a fluorescence emission spectrum having nearly the same shape but significantly reduced intensity was observed (lower dashed line). The reduced intensity presumably results from the quenching effect of iron. When the DXR-Fe(III) complex was added to DMPC SUVs, less quenching effect was observed, as evidenced by a fluorescence emission spectrum which was intermediate in intensity between that of the free drug and the DXR-Fe(III) complex in solution (lower solid line). The same emission spectra for DXR-Fe(III) complex in association with liposomes was observed whether iron was added before or after drug binding to the liposomes, indicating that the drug-iron complex forms readily with lipid-bound drug.

Of interest with respect to the present invention was the finding that DXR undergoes relatively rapid and irreversible chemical modification when complexed with ferric iron in the presence of SUVs formed with saturated and/or unsaturated phospholipids. One measure of this modification is a change in the 590/560 nm ratio of the fluorescence spectra, which would result from modification of the antracene ring. The 590/560 nm ratio of DSR-Fe(III) in association with DMPC is initially about 1.9. In the presence of ferric iron, at an iron:drug ratio of 2:1, this ratio falls to about 0.9 over a five hour period at 30° C. With a large molar excess of ferric iron, the decline in 590/560 is significantly faster, decreasing to less that 0.8 in two hours. The modified DXR, when extracted from the liposomes, has a 590/560 ratio of about 0.6. The modified drug also shows increased hydrophobicity, as evidenced by its partitioning characteristics in a standard biphasic partition system. This change may be due to cleavage of the more hydrophilic sugar moiety from the antrancene ring structure. It is noted that the drug modification reactions occur either in the presence or absence of oxygen, in liposomes composed either of saturated or unsaturated phospholipids. That is, the events leading to drug modification do not appear to require oxygen dependent electron transfer or free radical formation involving unsaturated lipids. However, as will be seen below, both oxygen and unsaturated lipids do contribute to drug modification in the drug/liposome formulation, and under these conditions, significant lipid peroxidative damage may also occur. One of the important aspects of the formulation of the invention, as will be seen below, is a significant reduction in such drug and lipid modifications.

B. Lipid Components

The liposomes in the composition are formed from standard vesicle-forming lipids, which generally include neutral and negatively charged phospholipids and a sterol, such as cholesterol. The selection of lipids is guided by considerations of (a) drug-release rate in serum, (b) drug-entrapment efficiency, (c) liposome toxicity, and (d) biodistribution and targeting properties.

Considering the effect of lipid components on in vivo drug-release rates, the most important compositional factors are chain length, degree of unsaturation, and head group charge and side groups in the phospholipids. The dependence of drug release rate on lipid composition is due in part to differences in the rate of exchange of amphipathic drug with the outer liposome bilayer, and in part to the differing stability of liposomes having different lipid compositions. From studies below, it will be seen that negatively charged phospholipids, such as phosphatidylglycerol (PG) and phosphatidylserine (PS), tend to enhance drug liposome stability as measured by DXR release in 50% plasma, whereas cardiolipin (CL) produces a marked destabilizing effect on the liposomes. The latter effect may be related to the apparently strong interaction between DXR and cardiolipin which is reflected by drug and lipid cross-linking which also occur in vivo (Goormaghtigh 1983). Neutral phospholipids, particularly phosphatidylcholine (PC), and negatively charged phospholipids, such as PG, PS, and phosphatidylinositol (PI), having acyl chain components of selected chain lengths and degree of saturation are available from commercial sources, or can be prepared by known techniques.

Another lipid component which is important to liposome stability, and therefore to drug-release rate, is cholesterol. In one study conducted in support of the present invention, the in vitro release of DXR from liposomes whose lipid components contained varying amounts of cholesterol, PC, and PG, PS, or CL, was examined. The liposomes were prepared substantially as described in Example I below, but contained the mole percentages of PC, PG, and cholesterol indicated in Table III below. Prior to each a test, the liposome suspensions were freed of free (soluble) drug by molecular sieve chromatography. The DXR/liposome compositions were each incubated at 37° C. for 1 hour in the presence of 50% human plasma, and the liposome-associated drug then separated from released, soluble drug, either by molecular sieve chromatography or ultracentrifugation. The amount of DXR retained in the liposomes was calculated as a percentage of the total original drug. The results are shown in Table III:

TABLE III

| Liposome Composition | Mole Ratio | % Liposome-Retained DXR |
| --- | --- | --- |
| PC:CHOL (DXR) | 4:4 | 72 |
| PC:CHOL (DXR) | 4:2 | 62 |
| PC:CHOL (DXR) | 4:1 | 76 |
| PC:CHOL (DXR) | 4:0 | 29 |
| PG:PC:CHOL (DXR) | 3:7:5 | 99 |
| PG:PC:CHOL (DXR) | 3:7:4 | 96 |
| PG:PC:CHOL (DXR) | 3:7:2.5 | 81 |
| PG:PC:CHOL (DXR) | 3:7:0 | 70 |
| PS:PC:CHOL (DXR) | 3:7:10 | 98 |
| PS:PC:CHOL (DXR) | 3:7:0 | 62 |
| CL:PC:CHOL (DXR) | 1:4:5 | 39 |
| CL:PC:CHOL (DXR) | 1:4:0 | 28 |

As seen from the table, 20 mole percent cholesterol produces a 2-fold to 3-fold enhancement in drug retention in PC liposomes, although no additional improvement is seen up to a cholesterol mole ratio of 50%. In liposomes formed with 30 mole percent PG, good drug retention achieved in the absence of cholesterol, but progressively greater stability is observed with increasing amounts of cholesterol. PS, another negatively charged phospholipid, gives substantially the same result as found with PG. Additional studies not reported here indicate that the increased drug retention is seen over a range of negatively charged phospholipid of between about 10-40 mole percent. Interestingly, the presence of only 10 mole percent cardiolipin (diphosphatidylglycerol), which contains a double negatively charged head group, substantially eliminated the cholesterol effect, giving poor drug retention even at 50 mole percent cholesterol.

Drug-entrapment efficiency, another factor to be considered in selecting a lipid composition, refers to the total amount of drug which can be loaded into liposomes, expressed as a ratio of drug per mole per liposome lipid. High entrapment efficiency is desirable both in terms of preparation costs and for maximizing the amount of drug which can be delivered in liposomal form in a give volume of liposomes. Experiments conducted in support of the present invention have conducted in support of the present invention have examined the efficiency of DXR entrapment in both large and smaller, sonicated liposomes, and with a number of different lipid compositions. The liposome and lipid composition variables are shown in Table IV below. In this table, MLV refers to large multilamellar vesicles, which typically contain heterogeneous liposome sizes averaging between about 0.5-5 microns, and SUVs, to sonicated but unfractionated vesicles. The final entry is for vesicles which have been sonicated and fractionated to remove larger vesicles, yielding predominantly small liposomes which are designated SUV(F). DPPG and DPPC are abbreviations for dipalmitoyl PG and dipalmitoyl PC, respectively, as distinguished from PC and PG, which are derived from egg lipids and which contain a mixture of both saturated and unsaturated phospholipid components.

TABLE IV

| | | DXR Entrapment | |
| --- | --- | --- | --- |
| Liposome Composition | Mole Ratio | % Total | DXR/Phospholipids m mole/mole |
| MLV-PC:CHOL:DXR | 4:4:1 | 14 | 35 |
| MLV-PC:DXR | 4:1 | 10 | 26 |
| MLV-CL:PC:CHOL:DXR | 1:4:5:1 | 64 | 128 |
| MLV-CL:PC:DXR | 1:4:1 | 58 | 116 |
| MLV-PS:PC:CHOL:DXR | 3:7:10:2 | 59 | 129 |
| SUV-PC:CHOL:DXR | 10:10:1 | 15 | 16 |
| SUV-CL:PC:CHOL:DXR | 1:4:2:1 | 47 | 94 |
| SUV-CL:PC:CHOL:DXR | 1:4:5:1 | 45 | 90 |
| SUV-CL:CHOL:DXR | 10:5:2 | 90 | 180 |
| SUV-PS:PC:CHOL:DXR | 3:7:4:2 | 50 | 100 |
| SUV-PG:PC:CHOL:DXR | 3:7:4:2 | 61 | 128 |
| SUV-DPPG:PC:CHOL:DXR | 3:7:4:2 | 39 | 78 |
| SUV-DPPG:DPPC:CHOL:DXR | 3:7:4:2 | 28 | 56 |
| SUV(F)-PS:PC:CHOL:DXR | 3:7:4:2 | 25 | 50 |

The data relating to MLVs suggest that a negatively charged phospholipid—either CL or PS—is required for good entrapment efficiency, but that cholesterol has only a minor effect, if any, on drug entrapment. With SUVs, a similar increase in entrapment efficiency was observed with either CL or PG, or PS. Also, entrapment efficiency was relatively poor when saturated phospholipids (DPPG alone or with DPPC) were substituted for the more unsaturated egg lipids, and in the predominantly very small SUV(F) liposomes. The data in Tables III and IV, taken together, suggest that the optimal liposome composition, for obtaining both high entrapment efficiency and good drug retention in vitro (in serum plasma), contains between 10-40 mole percent negatively charged phospholipid, particularly PG, but excluding cardiolipin (CL); between 20-50 mole percent cholesterol; and at least about 40 mole percent of a natural phospholipid, such as PC. Within this range of lipid components, the degree of acyl chain saturation and chain length may be varied to achieve desired drug-release characteristics in vivo, although it would be expected that a composition containing a high percentage of saturated lipids would have a reduced drug entrapment efficiency.

Another important consideration in the choice of lipid components is the toxicity of the drug/liposome composition which is produced. Since the soluble drug is generally more toxic than liposome-entrapped drug, it is desirable that the liposomes have both good entrapment efficiency and good drug retention in vivo. The lipid composition factors which effect drug retention and entrapment are discussed above. In addition, the acyl chain composition of the lipids may produce toxicity effects which are unrelated to the amount of drug present in the liposomes. Experiment conducted in support of the present invention to asses the toxicity of empty liposomes (not containing entrapped drug) on laboratory animals gave the following results: (1) Liposomes composed predominantly of saturated lipids, such as DPPG and DPPC, were more toxic than liposomes formed from corresponding unsaturated phospholipids. (2) Although unsaturated lipids are less toxic, they are also much more susceptible to lipid peroxidation damage on storage, and liposomes with substantial lipid oxidation damage are considerably more toxic, in terms of $LD_{50}$ values, than corresponding fresh liposomes. Also, it would be expected that lipid oxidation damage would increase toxicity in a drug/liposome composition, through decreased drug retention. As will be seen, an important aspect of the invention involves reducing peroxidative damage to lipid and drug components of an anthraquinone/liposome composition by a combination of protective agents, and therefore the susceptibility of unsaturated lipids to oxidative damage is less of a concern. That is, the composition of the invention contributes to reduced toxicity, in part, by allowing the use of unsaturated lipids, which are both less toxic and show greater drug entrapment, without concomitant lipid peroxidative damage, which would increase toxicity effects.

Biodistribution and liposome targeting may be affected by liposome size, surface charge, and the presence of specific surface-bound molecules which act to target the liposomes to specific sites in the body. Of particular interest to the success of the present invention is the enhanced accumulation of drug/liposomes in certain target organs, such as liver and spleen, and the reduced accumulation in non-target organs, such as kidney and heart, where drug toxicity is largely localized. In accordance with one aspect of the invention, optimal biodistribution is achieved within a selected size range of liposomes, as discussed below with reference to liposome sizing.

C. Protective Agents

The interaction of an anthraquinone drug with ferric iron in the presence of lipid, and the chemical modification of the drug which can occur in vitro have been described in Section A. As noted there, the drug modification reaction occurred under anoxic conditions, and in the presence of saturated lipids only. In Section B it was seen that, for a number of reasons, natural phospholipids (containing both saturated and unsaturated phospholipids) are generally advantageous in the drug/lipid composition of the invention. Further, it is reasonable to expect that the preparation and handling of the composition will involve some exposure to molecular oxygen, so that oxidative and free radical reactions which involve unsaturated lipids and oxygen can also be expected to produce lipid and drug modifications in the composition. The present section examines the oxidative and free radical mechanisms which can lead to such drug and lipid modification and demonstrates how such modification reactions can be controlled to a great extent by including in the composition a combination of lipophilic and water-soluble protective agent which act at different points in peroxidation/free radical pathways.

Figure 3:
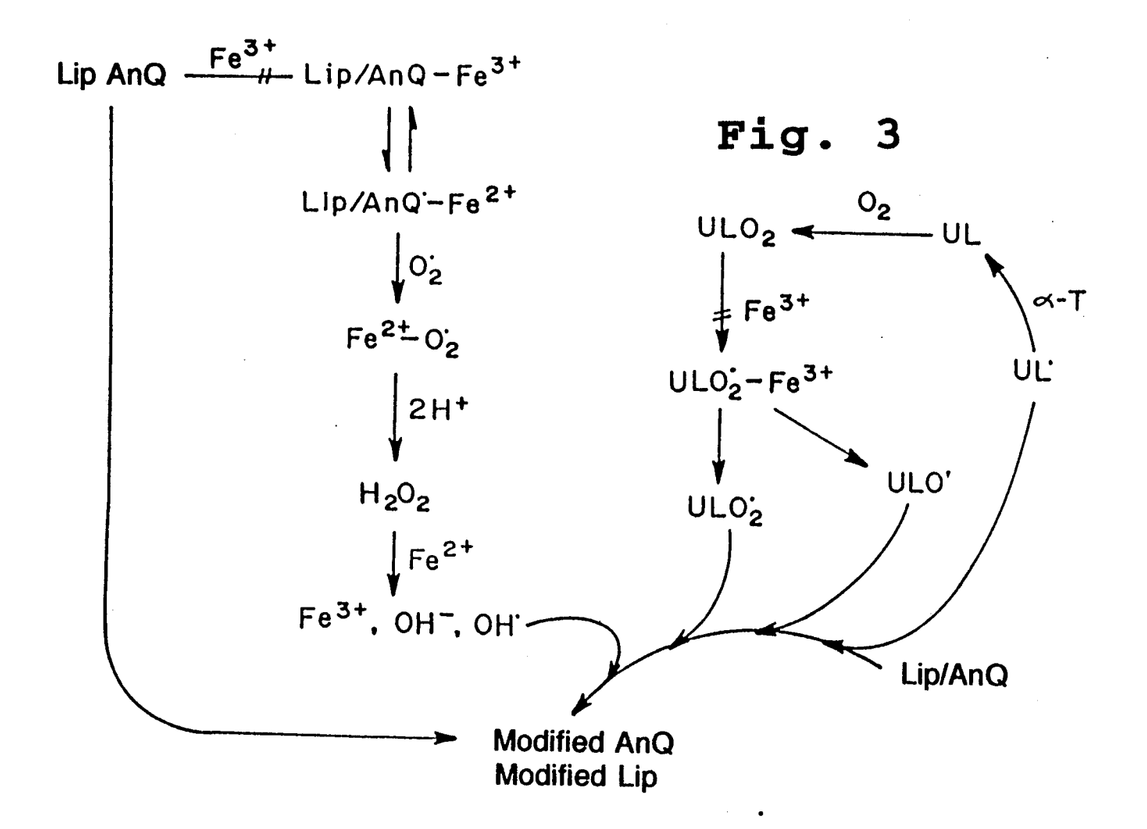
FIG. 3 illustrates oxidative and free radical mechanisms which may contribute to drug and lipid modifications in the presence of ferric iron, oxygen, and unsaturated lipids.

A scheme showing likely oxidative and free radical reactions in a composition containing an anthraquinone drug, lipid, and ferric iron is given in FIG. 3. Here, as in Section A, the liposome/anthraquinone formulation is indicated by Lip/AnQ; the acyl-chain lipid components forming the liposomes may be saturated, unsaturated, or a mixture of both. The upper left portion of the figure shows formation of the Lip/AnQ-Fe(III) complex, described in Section A. In the presence or absence of oxygen and either saturated or unsaturated lipid, the events leading to drug modification are likely to involve, first, possible formation of a semi-quinone-Fe(II) complex, and inter- or intramolecular free radical damage to the drug. Since the modified drug (DXR) is considerably more hydrophobic than the original molecule, it is possible that modification involves cleavage of the hydrophilic aminoglycoside residue from the anthracene ring. The reaction may also involve electron transfer from the semi-quinone to other functionalities in the ring structure, particularly to the hydroquinone groups, acting to delocalize the radical on the anthracene ring. The conversion of the AnQ-Fe(III) complex to modified drug is shown at the left in the figure.

Also as shown in the figure, the AnQ-Fe(II) complex can combine with molecular oxygen, leading to hydrogen peroxide formation, and ultimately hydroxyl radicals, which can then propagate free radical reactions. This oxygen-mediated pathway is suggested by earlier studies on the possible mechanisms of DXR-stimulated membrane damage in vivo where initial semi-quinone formation may occur by enzyme-catalyzed electron transfer (Goormaghtigh 1984), and, in vitro, where direct oxygen participation was involved (Gutteridge 1984a).

Where the liposomes contain an unsaturated lipid (UL), a separate pathway involving oxidation and free radical damage may also be involved, as illustrated at the right in FIG. 3. Initial reaction of the lipid with molecular oxygen leads to an oxygenated species which can complex with ferric iron, as indicated. The lipid complex, after undergoing a redox reaction to form an iron/lipid-radical complex, can form both peroxide and oxide lipid radicals, which in turn can propagate free radical reactions in the lipid and drug components of the composition, leading to drug and lipid modifications, as indicated. This pathway involving lipid oxidation and free radical propagation is suggested by studies on the mechanism of peroxidative damage in liposomal membranes (see, for example, Gutteridge 1984b and Sunamoto).

Heretofore, attempts to limit peroxidative damage in liposomes have focused on free radical scavenging, typically by including in the liposomes a lipophilic free radical scavenger, such as α-T. In theory, such free radical scavengers have the capacity to block free radical propagation in lipids and lipid-associated drugs, such as anthraquinones, and therefore to limit peroxidation-relative damage to that produced by "early" radical formation reactions. Assuming that the radical-forming events are relatively benign in comparison to free radical propagation, it would be expected that little additional protection, above that provided by α-T, could be obtained. Therefore an important aspect of the present invention is the discovery that significantly greater reduction in lipid and drug modification in an anthraquinone/liposome composition can be achieved by a combination of lipophilic free radical quencher and a water-soluble protective agent which acts at the level of free radical formation.

The lipophilic free radical scavenger used in the composition of the invention is preferably α-T, or a pharmacologically acceptable analog or ester thereof, such as α-T succinate. Other suitable free radical scavengers include butylated hydroxytoluene (BHT), propyl gallate (Augustin), and their pharmacologically acceptable salts and analogs. Additional lipophilic free radical quenchers which are acceptable for parenteral administration in humans, at an effective level in liposomes, may also be used. The free radical quencher is typically included in the lipid components used in preparing the liposomes, according to conventional procedures. Preferred concentrations of the protective compound are between about 0.2 and 2 mole percent of the total lipid components making up the liposomes; however, higher levels of the compound, particularly α-T or its succinate analog, are compatible with liposome stability and are pharmacologically acceptable.

The water soluble protective agent is an iron-specific chelating agent selected from the class of natural and synthetic trihydroxamic acids and characterized by a very high binding constant for ferric iron (on the order of $10^{30}$) and a relatively low binding constant for 2-valence cations, such as calcium and magnesium. A variety of trihydroxamic acids of natural origin have been described, including compounds in the ferrichrome class, such as ferrichrome, ferrichrome A, and albomycin; compounds in the ferrioxamine class, including the ferrioxamines and ferrimycines; and compounds in the fusaramine class. The structure and iron coordination properties of these compounds have been reviewed (Emery).

Figure 4:
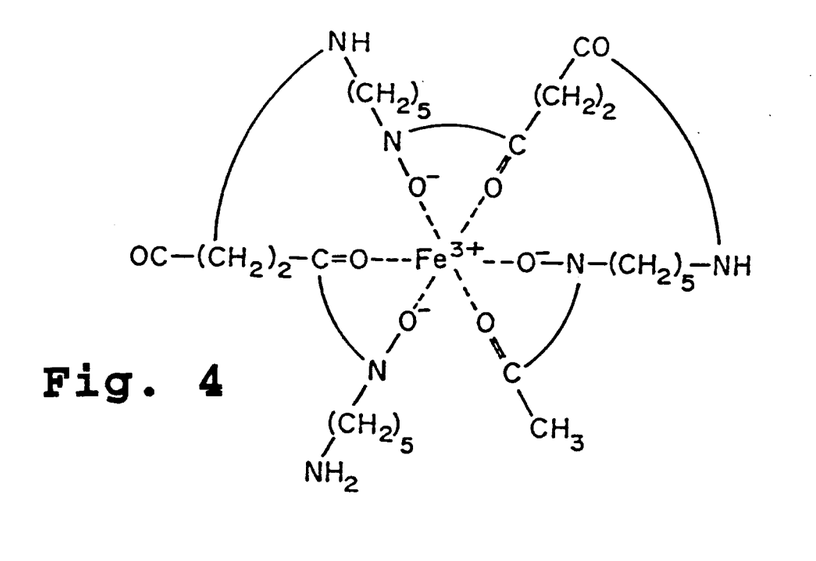
FIG. 4 illustrates ferric iron chelation by a trihydroxamic acid chelating agent.

One preferred chelator is ferrioxamine B, also known variously as ferrioxamine, deferoxamine, desferrioxamine B, and Desferal. This compound shows exceptional iron binding affinity and has been proven safe for parenteral use in humans in treating iron-storage disease and iron-poisoning (Keberle). The structure of iron-coordinated deferoxamine is shown in FIG. 4. As seen, the compound has three hydroxamic acid groups (—C(O)N(O)—) which can arrange octahedrally about the chelated iron, to form six symmetrical Fe-oxygen ligand bonds. The binding constants of ferrioxamine for iron and several 2-valence metals, including $Fe^{2+}$, are given in Table V.

TABLE V

| Metallic Ion | Binding Affinity |
| --- | --- |
| $Fe^{3+}$ | $10^{31}$ |
| $Ca^{2+}$ | $10^{2}$ |
| $Mg^{2+}$ | $10^{4}$ |
| $Sr^{2+}$ | $10$ |
| $Zn^{2+}$ | $10^{11}$ |

TABLE V-continued

| Metallic Ion | Binding Affinity |
| --- | --- |
| $Ni^{2+}$ | $10^{10}$ |
| $Co^{2+}$ | $10^{11}$ |
| $Cu^{2+}$ | $10^{14}$ |
| $Fe^{2+}$ | $10^{10}$ |

The chelating agent is present in the composition at a concentration which is in molar excess of the ferric iron in the liposome suspension. Typically, aqueous media used in liposome preparation contains at least about 1–2 μM ferric iron, and may contain up to 100 μM or more ferric iron. For aqueous medium containing up to about 20 μM iron, concentrations of chelating agent of about 50 μM are preferred.

The chelating agent is preferably added to vesicle-forming lipids at the time of liposome formation, so that the lipids are protected against drug-promoted lipid oxidation damage during liposome preparation. Methods for preparing liposomes by addition of an aqueous solution of chelating agent are described below. Here it is noted only that the liposome suspension formed by this method contains chelating agent both in the bulk aqueous phase and in the encapsulated form, i.e., within the aqueous internal liposome region. Alternatively the chelating agent may be included in the suspension after liposome formation.

Figure 5A:
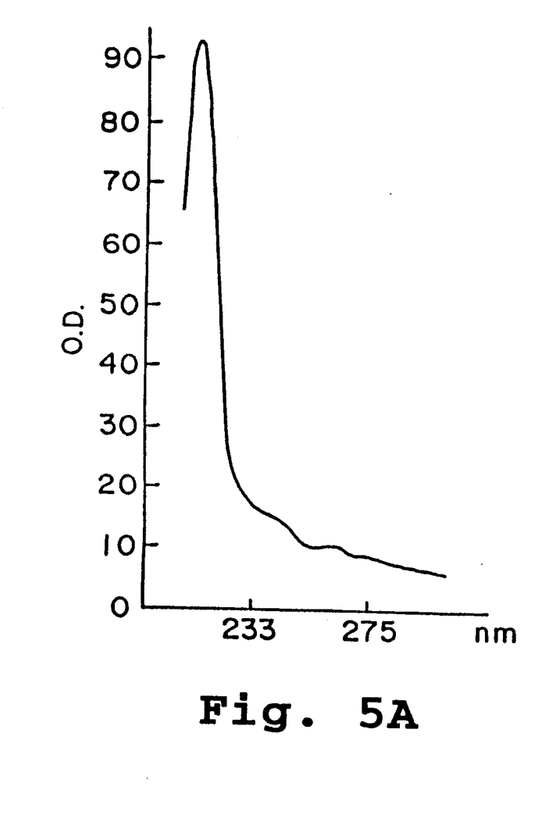
FIG. 5 shows UV spectra of lipids isolated from liposomes incubated in the presence (spectrum A) or absence (spectrum B) of ferrioxamine.
Figure 5B:
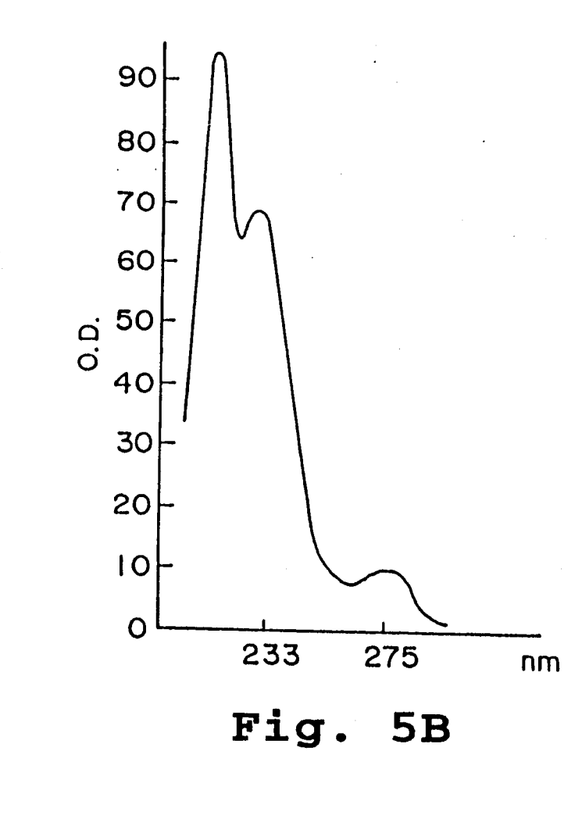
Figure 6:
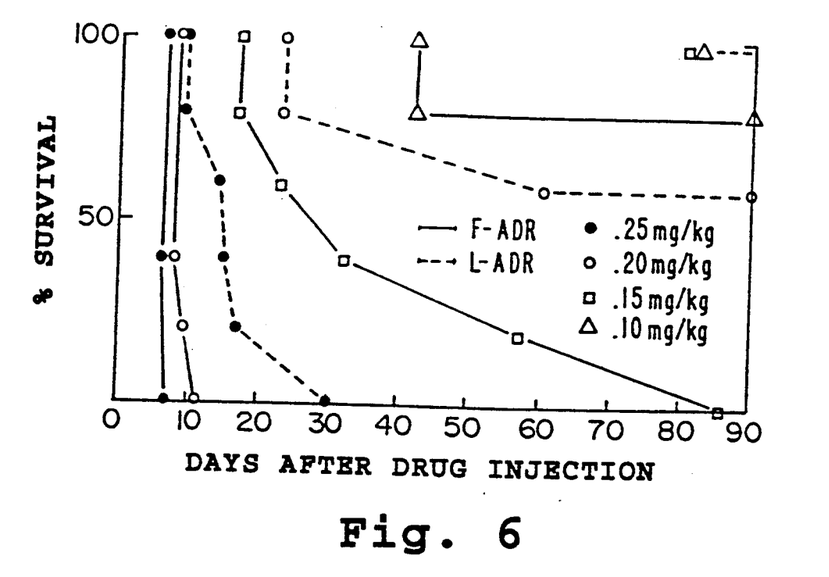
FIG. 6 plots the effects on survival in mice of graded doses of free DXR (F-DXR) and liposome-entrapped DXR (L-DXR) after a single injection.

Experiments conducted in support of the present invention have examined the degree of protection of lipid and drug components in a composition containing both α-T and ferrioxamine. In one study, liposomes containing DXR and α-T were prepared substantially as in Example I, either in the presence or absence of 50 μm ferrioxamine. The drug/liposome compositions was then stored under anoxic conditions for 1 day at 4° C., and the lipids were extracted conventionally by chloroform/methanol. The extracted lipids were dissolved in heptane and the UV spectra (190–300 nm) were monitored with a double-beam spectrophotometer. FIG. 5 shows the spectra obtained for lipids incubated in the presence (spectrum A) or absence (spectrum B) of chelator. The FIG. 5B spectrum shows strong peaks at about 233 nm, corresponding to conjugated diene formation and at about 275, corresponding to conjugated triene formation. The solid line spectrum in FIG. 5A shows little or no evidence of diene or triene formation, and spectral subtraction shows that diene and triene formation was inhibited more than about 99% in the ferrioxamine-containing composition.

In a second study, DXR/liposomes were prepared substantially as described in Example I, under nitrogen atmosphere or air, and in the presence or absence of α-T and ferrioxamine, as indicated in Table VI below. As in the experiment described above, the liposomes were composed of PG:PC:cholesterol, in a mole ratio of 3:7;4. α-T, when included, was present at a concentration of about 1.5 mole percent, and ferrioxamine, when included, was present at a concentration of 50 μM. The liposomes were stored under anoxic conditions for 1 day at 4° C., as above. Chemical modification of the drug was detected both by fluorescence emission spectroscopy and by assaying the change in drug toward a more lipophilic species, as described in Section A above.

TABLE VI

| Composition | | | αT (mole ratio) | Desferal (50 μm) | Air | Hydrophilic DXR % | Fluorescence Intensity Ratio (590/560 nm) |
|---|---|---|---|---|---|---|---|
| PG | PC | CHOL | | | | | |
| 3 | 7 | 4 | − | − | − | 67 ± 2 | 1.4 ± 0.1 |
| 3 | 7 | 4 | + | − | − | 68.1 ± 2 | 1.5 ± 0.1 |
| 3 | 7 | 4 | − | + | − | 67.1 ± 2 | 1.6 ± 0.1 |
| 3 | 7 | 4 | + | + | − | 86 ± 2 | 1.9 ± 0.1 |
| 3 | 7 | 4 | − | − | + | 47 ± 3 | 1.3 ± 0.1 |

The righthand column in Table VI shows the 590/560 nm fluorescence intensity ratios of the hydrophobic derivative of DXR for the five compositions. The data indicate two types of drug modification, as discussed above: (1) possible cleavage of the sugar moiety to give a more hydrophobic DXR product, and (2) damage to the anthracene ring which affects the 590/560 ratio of the drug. As will be recalled from section A, the 590/560 ratio is largest in unmodified DXR, and decreases with anthracene ring modification. The ratios observed show that α-T alone and ferrioxamine alone both gave moderate protections against drug modification, with ferrioxamine having a greater protective effect. Significantly, the combination of α-T and ferrioxamine provided much greater protection than either protective agent along, or what would be predicted from a sum of the two individual agent effects. The 1.9 value observed was substantially the same as that observed immediately after liposome preparation under nitrogen, indicating nearly complete protection of the drug through the storage period.

The studies just reported suggest that the protective mechanism of ferrioxamine is qualitatively different than that of α-T. It is likely that ferrioxamine acts primarily to inhibit peroxide generation and other "early" free-radical generating events, whereas α-T acts to quench free-radical reactions being propagated within the lipid bilayer. The likely points of inhibition by trihydroxamic acid chelator are indicated by double lines in FIG. 3.

The inhibitory effect of trihydroxamic acid chelation on peroxidation damage in liposomes is also in contrast to the peroxidation-stimulating effect observed when a conventional tetraacetic acid-type chelator, such as ethylenediaminetetraacetic acid (EDTA), is added to liposomes. The observed difference between trihydroxamic acid and tetraacetic acid chelators, in their ability to protect against peroxidative damage in liposomes, may be due to the difference in number of iron coordination sites available in the two species. Whereas a trihydroxamic chelator is able to form octahedral ligand bonding to all six ferric iron coordination sites, tetraacetic acid chelators are limited to four-site binding, leaving two iron coordinations sites available for participation in redox reactions. In this regard, it is noted that DTPA, a pentaacetic acid chelator, also shows a protective effect on anthraquinone modification in vitro, in the presence of lipids and ferric iron, suggesting that five-site coordination may also be effective in reducing iron participation in redox reactions.

D. Liposome Preparation

Methods for preparing drug-containing liposome suspensions generally follow conventional liposome preparation methods, such as those reviewed by Szoka et al. In one preferred method, vesicle-forming lipids are taken up in a suitable organic solvent or solvent system, and dried in vacuo or under an inert gas to a lipid film. The drug is preferably included in the lipids forming the film. The concentration of drug in the lipid solution is preferably in molar excess of the final maximum concentration of drug in the liposomes, to yield maximum drug entrapment in the liposomes. In preparing the liposome/DXR composition described in Example I, a film of lipids was hydrated with an aqueous suspension of DXR at a final drug-to-phospholipid concentration of about 2:10. This produced vesicles having a DXR concentration, after removal of free DXR, of about 10 mole percent.

The aqueous medium used in hydrating the dried lipid or lipid/drug is a physiologically compatible medium, and preferably pyrogen free physiological saline, such as is used for parenteral fluid replacement. The solution is mixed with a sterile solution of chelating agent, to a final desired chelator concentration, added to the film, and the lipids allowed to hydrate under rapid (with shaking) or slow (without shaking) conditions. The lipids hydrate to form a suspension of multilamellar vesicles (MLVs) whose sizes range typically between about 0.5 microns to 10 microns or greater. In general, the size distribution of MLVs in the above procedure can be shifted toward smaller sizes by hydrating the lipid film more rapidly, with shaking. The liposomes contain encapsulated chelating agent, at a concentration approximately equal to the bulk aqueous phase concentration.

E. Liposome Sizing

The liposome suspension may be sized to achieve a selective size distribution of vesicles in a size range less than about 1 micron and preferably between about 0.05 to 0.5 microns, and most preferably between about 0.05 and 0.2 microns. The sizing serves to eliminate larger liposomes and to produce a defined size range having optimal pharmacokinetic properties.

Several techniques are available for reducing the sizes and size heterogeneity of liposomes. Sonicating a liposome suspension either by bath or probe sonication produces a progressive size reduction down to small unilamellar vesicles (SUVs) less than about 0.05 microns in size. A sonicating procedure used in reducing liposome sizes to about 0.2 microns or less is described in Example I. Homogenization is another method which relies on shearing energy to fragment large liposomes into smaller ones. In a typical homogenization procedure, MLVs are recirculated through a standard emulsion homogenizer until selected liposome sizes, typically between about 0.1 and 0.5 microns, are observed. In both methods, the particle size distribution can be monitored by conventional laser-beam particle size discrimination.

Extrusion of liposomes through a small-pore polycarbonate membrane is an effective method for reducing liposome sizes down to a relatively well-defined size distribution whose average in the range between about 0.1 and 1 micron, depending on the pore size of the membrane. Typically, the suspension is cycled through the membrane several times until the desired liposome size distribution is achieved. The liposomes may be extruded through successively smaller-pore membranes, to achieve a gradual reduction in liposome size.

Centrifugation and molecular sieve chromatography are other methods which are available for producing a liposome suspension with particle sizes below a selected threshold less than 1 micron: These two methods both involve preferential removal of larger liposomes, rather than conversion of large particles to smaller ones. Liposome yields are correspondingly reduced.

Studies aimed at determining the biodistribution and drug clearance of DXR/liposomes as a function of liposome size have been conducted, and reported earlier by the inventors (Gabizon 1982, 1983). More recent studies conducted in support of the application looked at organ distribution of DXR 1, 5, and 24 hours after administration of DXR either in free form or in liposomes having median sizes of 35±14 nm or 115±25 nm. The results of the study are given in Table VII, where data on each time point represents an average of three animals. The organ weights, given in parentheses, are also calculated as an average of three animals.

TABLE VII

| Organ | DXR Delivery System | TIME (μg DXR/g tissue) | | |
|---|---|---|---|---|
| | | 1 hr | 5 hrs | 24 hrs |
| Liver | 115 nm vesicles | 44.9 | 37.1 | 16.7 |
| (1.46 g) | 35 nm vesicles | 39.2 | 16.8 | 4.0 |
| | Free | 30.5 | 16.4 | 3.8 |
| Spleen | 115 nm vesicles | 24.6 | 26.0 | 16.0 |
| (0.15 g) | 35 nm vesicles | 14.6 | 13.5 | 8.0 |
| | Free | 8.1 | 10.7 | 8.8 |
| Heart | 115 nm vesicles | 2.3 | 2.0 | 1.1 |
| (0.12 g) | Vw5nm Vesicles | 5.9 | 3.4 | 1.2 |
| | Free | 8.4 | 4.2 | 0.9 |
| Lungs | 115 nm vesicles | 4.3 | 3.8 | 2.3 |
| (0.16 g) | 35 nm vesicles | 8.9 | 6.9 | 3.1 |
| | Free | 13.2 | 8.6 | 3.6 |
| Intestine | 115 nm vesicles | 2.9 | 1.0 | 1.3 |
| | 35 nm vesicles | 6.3 | 5.6 | 2.8 |
| | Free | 5.8 | 3.1 | 1.9 |
| Kidney | 115 nm vesicles | 12.1 | 6.0 | 3.8 |
| (0.22 g) | 35 nm vesicles | 26.4 | 13.6 | 6.0 |
| | Free | 31.9 | 19.4 | 6.9 |
| Skeletal | 115 nm vesicles | 0.47 | 3.7 | 0.36 |
| Muscle | 35 nm vesicles | 1.6 | 1.1 | 0.69 |
| (—) | Free | 2.3 | 2.8 | 0.59 |

The data in Table VII show that liposomes, and particularly the 115 nm liposomes, show increased drug levels in the liver and spleen and decreased drug levels in heart, lung, intestine, kidney, and skeletal muscles when compared with the free drug. The liposomes are thus particularly advantageous in treating liver- and spleen-localized tumors and in reducing toxicity related to drug levels in non-target tissues, particularly the heart. Another important advantage of 115 nm liposomes which is seen from the data is slower drug clearance in liver and spleen tissue. The drug clearance in animals which received the smaller (35 nm) liposomes more closely followed that of the free drug. The improved biodistribution and longer clearance times observed with the 115 nm vesicles are observed in the liposome size range down to about 0.05 microns. Below this range, drug distribution and clearance characteristics begin to approximate those of the free drug, as seen.

For a variety of reasons, the optimal upper size limit of the liposomes is about 0.5 microns and, preferably, about 0.2 microns. First, the desired target tissue regions, such as liver sinusoids and parenchyma, spleen, and bone marrow are more accessible to liposomes smaller than about 0.2 microns. Secondly, liposomes in the 0.2 micron size range can be readily sterilized by filtration through a depth filter. Smaller vesicles also show less tendency to aggregate on storage, thus reducing a potentially serious problem when the composition is administered parenterally. Finally, liposomes which have been sized down to the submicron range show more uniform biodistribution and drug clearance characteristics, since they have more uniform sizes.

F. Removing Free Drug

Free drug, i.e., drug present in the bulk aqueous phase of the medium, is preferably removed to increase the ratio of liposome-entrapped to free drug. This is particularly useful if the liposomes have been prepared under conditions of excess drug, to maximize drug/lipid ratios in the liposomes. Under the preparation conditions described in Example I, for example, the liposomes incorporated between about 50–60% of the total DXR added initially, leaving 40–50% free DXR. The drug removal is designed to reduce the final concentration of free to less than about 20% and preferably, less than about 10% of the total drug present in the composition.

Several methods are available for removing free anthraquinone drug from a liposome suspension. As indicated above, the sized liposome suspension can be pelleted by high-speed centrifugation, leaving free drug and very small liposomes in the supernatant. Another method involves concentrating the suspension by ultrafiltration, then resuspending the concentrated liposomes in a drug-free replacement medium. Alternatively, gel filtration can be used to separate larger liposome particles from solute (free drug) molecules. Of course, it is necessary to include the chelating agent in the elution buffer, or add chelating agent to the eluted liposomes, since the gel matrix itself will remove the chelation agent from the original suspension.

One preferred procedure for removing free drug utilizes an ion-exchange resin capable of binding drug in free, but not in liposome-bound, form. With DXR, the preferred resin is a cation-exchanger, since the drug is positively charged at neutral pH. One advantage of the ion-exchange approach is that free drug can be removed in line during drug administration, as the drug composition flows from a container to the site of injection. This system has the advantage that essentially all of the free drug can be removed from the suspension, and the liposomes administered before drug leakage from the liposome to the aqueous bulk phase occurs. The system may also be effective in removing free pyrogens, with proper selection of resin(s).

II. Therapeutic Uses in Tumor Treatment

Studies by the inventors, discussed above, have shown that small, drug-carrying liposomes can concentrate liposome-associated drug in tissue regions, such as liver sinusoids and parenchyma, spleen, and bone marrow which are accessible to small liposomes (less than about 0.2 microns in size). These findings having important implications for treating metastatic diseases of the liver, primary hepatomas, lymphoid proliferative diseases, and leukemias, all of which are major cancers, both in terms of numbers and geographic distribution.

One of the most effective anti-tumor drugs, and a drug of choice in many instances, is DXR, a related anthracycline glycoside compound, or mitoxanthrone. For these anthraquinone drugs, the challenge for improved anti-tumor therapy is to decrease the toxicity of the liposome therapeutic composition without compromising the therapeutic effect of the drug. With regard to DXR, which has a very specific toxicity for the heart muscle, the inventors have shown that a DXR/liposome composition, properly formulated, can significantly decrease the uptake of drug by the heart muscle and reduce the severity of the histopathological changes seen in mice treated with similar doses of free DXR.

Another source of toxicity is oxidative damage to the lipid and drug components of the liposome composition. As demonstrated in Section I, anthraquinone drugs actively promote peroxidative reactions in the presence of lipids, leading to significant modification of both lipid and drug components in the drug/liposome composition. The modified composition is more toxic, due to the peroxidative damage to lipids and increased drug leakage, and the drug itself may lose therapeutic effectiveness with modification.

The toxicity and therapeutic effectiveness of a DXR/liposome composition (L-DXR) prepared according to the invention is examined in Examples II–IV. Example II show that significantly higher doses of DXR in liposomal form can be administered without lethality. The results are summarized in FIG. 7. Example III, which looks at the effects of repeated administration of graded doses of free drug (F-DXR) and L-DXR finds significant reduction in (a) lethality, (b) loss of body weight, (c) changes in blood cholesterol and triglyceride levels, and (d) organ pathology when L-DXR treatment is compared with F-DXR.

Clinical trials using L-DXR to treat patients suffering from various types of cancer, including metastatic and primary liver cancer, are in progress. The treatment results are summarized in Example IV. The findings to date indicate a significant improvement in overall patient comfort, due to virtually complete elimination of gastrointestinal toxicity (nausea, vomiting, diarrhea, and stomatitis), and no pain at the site of injection. The results represent a major improvement in treatment of certain cancers with anthracycline glycosides.

The following examples, which describe various therapeutic uses and features of the invention, are intended to illustrate, but not limit, the invention.

Materials

Adriamycin (doxorubicin HCl, containing lactose) was obtained from Farmitalia (Milano, Italy); phospholipids (chromatographically tested, greater than 99% purity) from Lipid Products (Surrey, England) or Avanti Lipids (Birmingham, Ala.); cholesterol (chromatographically tested, greater than 99% purity); physiologic saline solution, from Baxter Travenol (Ashdod, Israel); ferrioxamine (Desferal), from Ciba-Geigy (Basel, Switzerland); and ($\alpha$-T), from Sigma Chemicals (St. Louis, Mo.).

EXAMPLE I

Preparation of Liposome-Entrapped DXR (L-DXR)

A solution of vesicle-forming lipids contained 360 mg cholesterol, 33 mg $\alpha$-T, 1750 mg egg PC, and 750 mg PG (egg, sodium salt) in 100 ml chloroform. The mole ratio of lipid components was PC:PG:cholesterol (7:3:4). The solution was divided, added to two 500 ml round-bottom flasks, and evaporated under vacuum in a rotary evaporator. Further removal of organic solvents and drying of the film was accomplished by lyophilization in a lyophilizer at 150 mTorr pressure overnight.

A drug solution contained 300 mg DXR (6 vials containing 50 mg doxorubicin HCl and 250 mg lactose each) dissolved in saline (sterile, pyrogen-free physiologic NaCl solution) containing ferrioxamine ($\sim$50 $\mu$M). The final solution contained DXR at 5 mg/ml, and ferrioxamine at 30 $\mu$g/ml in a total volume of 60 ml. The DXR solution was added to round-bottom flasks containing the lipid films (30 ml/flask). This initial phospholipid-to-DXR molar ratio was 10:2. The mixture was vortexed, then equilibrated in a shaking device at 100 stroke/min for 2 hr at 15°–20° C.

The multilamellar vesicle (MLV) dispersion obtained was sonicated by ultrasonic irradiation using a $\frac{1}{2}$-in sapphire-bonded probe, with pulse sonication during 15 min (60%, or 9 minute, sonication time) under optimal output conditions. Sonication was carried out under a stream of nitrogen (or argon) with the vessel immersed in ice water. The sonication procedure was standardized by determining the optical density of the dispersion at 380 nm wavelength. Specifically, the sonication was carried out until a 1:100 dilution of the dispersion in saline gave an O.D. value of less than 0.9. If the O.D. was greater than 0.9, the sonication was continued for an additional 3 min. Starting O.D. values of the MLV dispersions are in the range of 1.300–1.500. The sonicated dispersions were centrifuged in a bench-top centrifuge (2,000 rpm, 10 min) to remove large titanium particles. Alternatively, the liposomes were extruded several times through 0.2 $\mu$m pore polycarbonate membrane until an O.D. value of less than 0.9 was obtained. Free drug was removed by ultracentrifugation. The sized liposomes were sterilized by filtration through a 0.2 micron polycarbonate filter.

The sterilized liposomes were stored in vacuum-sealed sterile glass bottles at 4° C. in the dark. The DXR-containing liposomes (L-DXR) had the following characteristics:

(a) Total DXR in the liposomes was greater than 50% of the initial amount of drug;

(b) Phospholipid concentration (determined by organic phosphate present) was 10–13 $\mu$mole/ml;

(c) The amount of free DXR (determined by DXR/phospholipid molar ratio before and after passage through Sephadex G-50 column was less than 5% of the total DXR;

(d) The size distribution was between 0.05 and 0.2 microns;

(e) Lipid oxidation (determined by a modification of the method of Klein) was less than 1% of total phospholipid, based on the abnormal spectral absorbance at 233 nm, due to diene conjugation;

(f) Stability in human plasma (measured by DXR retention in DXR liposomes in 50% plasma at 37° C. for 1 hour) was greater than 80%;

(g) The liposomes were sterile, as determined by addition (3–4 ml) of the liposome suspension in Bactec 7-ml bottles (aerobic and anaerobic microbiological cultures) for 7 days; and (h) The rabbit pyrogenicity test was negative.

EXAMPLE II

Single Injection Survival with Graded Doses of F-DXR and L-DXR

L-DXR was prepared as in Example I, to final DXR concentrations of 1, 1.5, 2, and 2.5 mg/ml, with corresponding phospholipid concentrations of 16, 24, 32, and 40 µmole/ml, respectively, and cholesterol concentrations of 6.4, 9.6, 12.8, and 16 µmole/ml, respectively. Free DXR (F-DXR) was prepared in sterile, pyrogen-free physiologic saline solution to final concentrations of 1, 1.5, 2, and 2.5 mg/ml.

Figure 7:
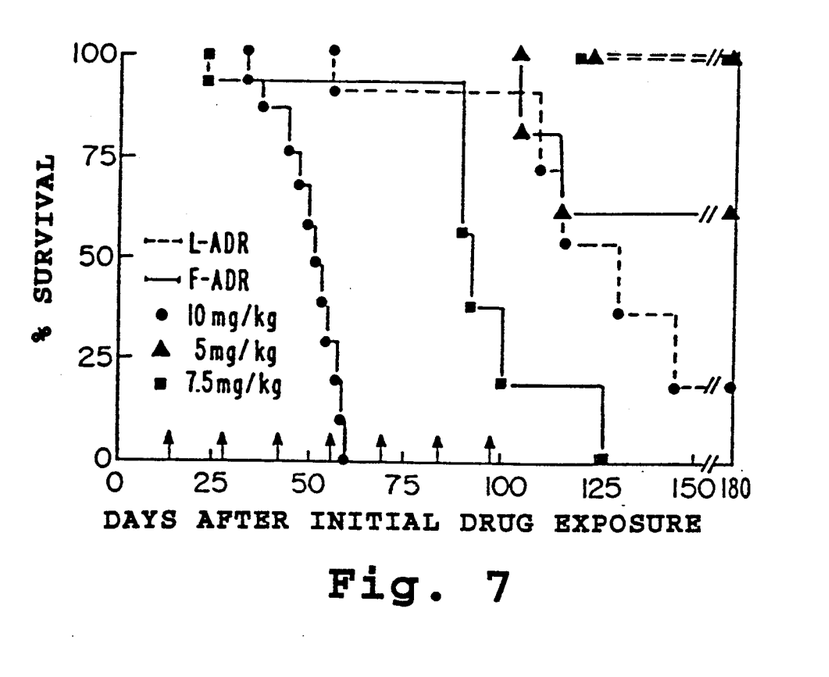
FIGS. 7 and 8 are plots of the survival curves for male and female mice, respectively, after repeated administration of graded doses of F-DXR and L-DXR.

BALB/c male mice were treated intravenously with 4 different doses of F-DXR and L-DXR: 10, 15, 20, and 25 mg/kg, by administering about 1% total animal weight of the corresponding F-DXR or L-DXR formulation. The survival curve recorded for a period of 90 days is shown in FIG. 7. As seen, there is a marked decrease in toxicity of the drug in the liposome-encapsulated form. No mortality was registered among animals treated with 15 and 10 mg/kg of L-DXR and 60% of the mice injected with 20 mg/kg survived throughout 90 days. F-DXR caused 100% of mortality in the groups injected with 25, 20, and 15 mg/kg and 20% mortality in the group receiving 10 mg/kg.

The pattern of mortality was a mixed one for some mice, especially those from the high-dose treated groups, dying within the first two weeks after injection (one month in the case of the 25 mg/kg L-DXR treated group), and other mice dying with a significant delay of 6-7 weeks or more after drug administration. Autopsy of mice dying in the acute phase showed severe gastrointestinal toxicity with hypersecretion and dilation o the intestinal loops, while in those mice dying in the delayed phase, the most significant findings were decrease of body weight and hypotrophy of the abdominal organs.

EXAMPLE III

Effects of Repeated Administration of Graded Doses of F-DXR and L-DXR

L-DXR was prepared as in Example I, to final DXR concentrations of 0.5, 0.75, and 1.0 mg/ml, corresponding to phospholipid concentrations of 8, 12, and 16 µmole/ml, respectively, and cholesterol concentrations of 3.2, 4.8, and 6.4 µmole/ml, respectively. Free DXR (F-DXR) was prepared in sterile, pyrogen-free physiologic saline solution to final concentrations of 0.5, 0.75, and 1 mg/ml.

Sabra mice were divided into groups of 15 mice. Three different doses of either F-DXR or L-DXR were tested: 5, 7.5, and 10 mg/kg body weight. Each dose level was tested on 15 male and 15 female mice. Treatment was administered as a bolus injection through the tail vein on days 0, 14, 28, 42, 56, 70, 84, and 98 of the experiment. The pulsed injection scheme was used for the purpose of achieving high cumulative doses, prolonging the period of exposure of the animals to the drug, and mimicking the way DXR is usually administered in clinical practice. In view of the toxicity observed after single injection (Example XI), DXR was administered at a maximum 10 mg/kg dosage so that the occurrence of acute toxicity would be reduced or nil. In order to avoid the overlapping myelosuppression of successive treatment, 14 days were allowed between successive injections, based on previous observations that full regeneration of the activity of myeloid centers in the spleen after treatment with 10 mg/kg of DXR occurred between 7-12 days after drug administration.

During the course of the experiment, mice were inspected daily and survival curves were recorded. Whenever possible, dead mice were autopsied and a limited sample of organs sent for histopathological examination. Blood counts and body weights were checked weekly. The blood counts were done in a Coulter analyzer with a 20 µl sample obtained from the retro-orbital blood sinuses. One-third of the mice of each group were sacrificed on day 42, after 3 injections. A second third was sacrificed on day 84, after 6 injections. The remaining mice were sacrificed on day 180, 82 days after the 8the and last injection. Before sacrifice, the mice were bled under light ether anesthesia to obtain serum for the biochemical tests. The animals were then dissected and the removed organs, after weighing, were fixed in Bouin's solution and processed for light microscopy examination with hematoxylin-eosin-phosphomolybdic acid: light green stain.

Figure 8:
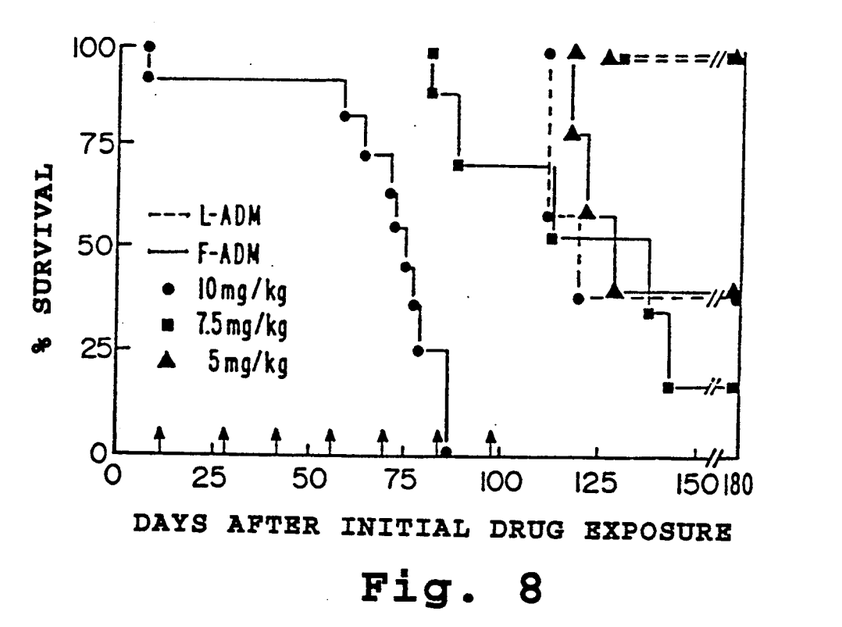

(a) Effects on Survival. The survival curves of male and female mice are shown in FIGS. 8 and 9. Significant mortality rates were observed in all the groups infected with free drug. By contrast, 100% survival after 180 days was found in the groups injected with the intermediate (7.5 mg/kg) and low dose (5 mg/kg) of L-DXR. The high dose (10 mg/ml) of L-DXR caused a substantial rate of mortality, although a minor group of the animals survived a cumulative dose of DXR of 80 mg/kg. There was a slight trend towards higher toxicity in male as compared to female mice with the high and intermediate dosages of F-DXR.

(b) Effects on Peripheral Blood Counts. Blood counts taken 7 and 14 days after each injection showed minor reductions only in the white cell count. There were no significant differences between the F-DXR and the L-DXR treated groups. The hemoglobin concentration was not appreciably affected during the course of the experiment.

(c) Effects on Body and Organ Weights. Table II shows the effect on body and organ weights of repeated administration of F-DXR or L-DXR, at a 10 mg/kg dosage level. The weight measurements were made 42, 84, and 180 days after initial drug injection. The body and organ weights are expressed in percent relative to untreated mice. The percent survivors at each of the three time points is indicated at the top in the table; the dashes (—) indicate no survivors.

When the weights of liver, spleen, kidneys, and heart of the different experimental groups are compared, it is apparent that the F-DXR caused a substantial weight reduction notice.·ble after 3 injections (day 42) and 6 injections (day 84). L-DXR treatment caused no significant decrease of organ weights, except in male mice on day 180.

Unlike the acute toxicity deaths observed in the animals injected with single high doses of DXR (Example XI), the deaths observed with the multiple injection regime were generally characterized by a decrease of body weight with disappearance of abdominal and subcutaneous fat, organ shrinkage, and lack of gastrointestinal toxicity. The lower the dose received, the less pronounced were the body and organ weight reductions of dead mice. All male and female mice which received multiple doses at 7.5 or 5 mg/kg L-DXR survived to day 180. Animals dying after treatment with 7.5 and 5 mg/kg of F-DXR frequently exhibited pleural and peritoneal effusions, cardiomegaly, and lung congestion. A finding noticed only in mice treated with F-DXR, 10 mg/kg, was a marked weakness of the lower limbs unexplained by the histopathological finding in skeletal muscle and which could be related to a neuropathic effect.

TABLE VIII

| | Percent Body and Organ Weight | | | | | |
|---|---|---|---|---|---|---|
| | DAYS AFTER 1st INJECTION | | | | | |
| | Male | | | Female | | |
| | 42 | 84 | 180 | 42 | 84 | 180 |
| % Surviving | | | | | | |
| F-DXR | 87 | — | — | 93 | 27 | — |
| L-DXR | 100 | 90 | 18 | 100 | 100 | 40 |
| Body | | | | | | |
| F-DXR | 75 | — | — | 95 | 84 | — |
| L-DXR | 96 | 94 | 69 | 97 | 96 | 83 |
| Liver | | | | | | |
| F-DXR | 75 | — | — | 107 | 91 | — |
| L-DXR | 96 | 101 | 88 | 91 | 103 | 99 |
| Spleen | | | | | | |
| F-DXR | 71 | — | — | 78 | 67 | — |
| L-DXR | 80 | 88 | 131 | 78 | 91 | 101 |
| Kidneys | | | | | | |
| F-DXR | 76 | — | — | 78 | 91 | — |
| L-DXR | 87 | 81 | 66 | 93 | 100 | 84 |
| Heart | | | | | | |
| F-DXR | 82 | — | — | 97 | 74 | — |
| L-DXR | 90 | 105 | 71 | 91 | 91 | 93 | d) Effects on Blood Biochemistry Values. Blood levels of glucose, cholesterol, triglycerides, urea, uric acid, creatine, and total protein were measured at 42, 84, and 180 day time points. Blood enzyme levels of alkaline phosphatase, aspartate aminotransferase, and alanine aminotransferase were also assayed at these time points.

The most important differences in blood chemistry between F-DXR and L-DXR administration occurred in blood glucose, cholesterol, and triglyceride levels. These differences are seen in Table III below, which gives data on female mice receiving 10 mg/kg of either F-DXR or L-DXR. Glucose, cholesterol, and triglyceride levels are expressed as percent control (untreated) animals, and "nm" means "not measured".

As seen, animals treated with free drug show decreased blood glucose, hypercholesterolemia, and hyperglyceridemia. By contrast, reduced blood glucose was seen only at 180 days for L-DXR treatment, and elevated cholesterol and triglyceride levels were not observed even at 180 days.

Although not shown in the table, it is also noted that animals receiving lower free drug dosages (7.5 and 5 mg/kg) showed increased creatine levels at 180 days, indicating serious renal function impairment. Increased levels of creatine were not observed in L-DXR treated mice, even at 10 mg/kg doses.

Increased liver enzymes—alkaline phosphatase and aminotransferases—were observed in animals treated with either F-DXR or L-DXR, although in both experimental groups a drop in alanine aminotransferase occurred at 180 days.

TABLE IX

| | Change in Blood Chemistry | | |
|---|---|---|---|
| | DAYS AFTER 1st INJECTION | | |
| | 42 | 84 | 180 |
| % Surviving | | | |
| F-DXR | 93 | 27 | — |
| L-DXR | 100 | 100 | 100 |
| Glucose | | | |
| F-DXR | 97 | 57 | — |
| L-DXR | 113 | 98 | 50 |
| Cholesterol | | | |
| F-DXR | 300 | 383 | — |
| L-DXR | 79 | 93 | 111 |
| Triglyceride | | | |
| F-DXR | nm | 416 | — |
| L-DXR | nm | 123 | 105 |

(e) Effects on Tissue Pathology. The histopathological examinations showed reduced pathological damage, especially in kidney, heart, and ovaries in animals receiving L-DXR, compared with free drug administration.

EXAMPLE IV

Clinical Trials With L-DXR

Eight cancer patients have been treated with the L-DXR composition of Example III. The administration of the drug was done using a 120 ml "Voluset" at a concentration of approximately 0.5 mg/ml in isotonic saline and at a rate of 2-3 ml per min. For intraarterial injections, peristaltic pumps were used, with the rate of infusion being ~1.5 ml/min. Two patients have had the liposomal drug delivered intraarterially into the liver, without any side effects. This was done taking advantage of previously implanted pumps. In both patients, the perfusion of the liver with the pump was previously examined with a Tc-99 labeled macroaggregated albumin scan.

Transient myelosuppression affecting the white blood cell count was observed in two patients: patient #3 (Table IV), after receiving the third dose (highest dose given, 100 mg DXR) and patient #6 (pretreated with X-irradiation and with 5-fluorouracil, and Mitomycin-C) after 80 mg DXR. The nadir for patient #3 was 1,900 cells/mm$^3$, and for patient #6, 2,300 cells/mm$^3$.

Hair loss was significant in only 50% of the patients. Fever related to the administration of L-DXR from pyrogen-free batches was observed in two instances. The temperature rise was preceded by chills and reached 39° C. to 40° C. It occurred several hours after the treatment. In both cases, it was self-remitting. With one of the two patients fever was a constant feature after administration of F-DXR. No gastrointestinal toxicity, neither immediate (nausea, vomiting, diarrhea) nor delayed (stomatitis) was observed in any of the patients. Electrocardiographic changes were not observed after treatment. No local pain in the site of injection was noticed by any patient.

In a patient suffering from hepatoma and having failed previously with several drugs, including DXR, L-DXR injected intraarterially brought about a significant shrinkage of the liver tumor. Cumulative details on the treated patients is presented in Table X below.

While examplary embodiments of an anthraquinone/liposome composition and its uses have been described herein, it will be appreciated that various changes and modifications can be made without departing from the invention.

TABLE X

| Patient No. | Age | Diagnosis | Treatment Date | Batch no. | Dose (mg ADM) | Present Disease Status |
|---|---|---|---|---|---|---|
| 1 | 36 | Hepatoma | 2/2 | 1 | 25 | Died from progressive disease (4/17) |
| 2 | 45 | Colon ca. | 3/17 | 2 | 30 | Jaundice, cirrhosis (most probably post-radiation), dropped from the protocol (1). |
| 3 | 64 | Colon ca. | 7/21 (1) | 5 | 35 | Presently undergoing reevaluation. |
|   |   |   | 8/2 (2) | 6 | 60 |   |
|   |   |   | 9/1 (3) |   | 100 |   |
| 4 | 63 | Small cell ca. of lung | 7/22 | 5 | 42 | Died (8/2) from massive intrapleural bleeding and bulky lung tumor. |
| 5 | 29 | Hepatoma | 8/22 (1) | 6 | 75 | Previous failure to free DXR, receives hepatic intraarterial treatment. Little subjective improvement. Significant reduction in Alkaline Phosphatase (1200 → 400 units!) (2) |
|   |   |   | 9/19 (20) | 8 | 95 |   |
| 6 | 62 | Rectum ca. | 8/23 (1) | 7 | 80 | Stable Karnofsky status and stable liver function tests. |
|   |   |   | 9/9 (2) | 8 | 50 |   |
| 7 | 66 | Colon ca. | 9/6 | 6 | 25 | Hapatic intraarterial treatment. Dose reduction due to jaundice (3). |
| 8 | 58 | Hepatoma | 9/19 | 8 | 78 | After failure to free Adriamycin. Not yet evaluable. |

It is claimed:

1. A method of treating liver neoplasms in a human patient with at least the same extent of therapeutic effectiveness, but with substantially reduced incidence of alopecia and nausea with respect to that produced by treatment with doxorubicin in free form, comprising preparing, for parenteral administration, an aqueous suspension of liposomes (i) whose lipid bilayer region contains at least about 2.5 mole percent of doxorubicin or a pharmacologically acceptable salt thereof, and (ii) which are sized to allow for sterilization by filtration through a 0.45 micron pore size membrane, and which suspension contains less than about 20% doxorubicin in free-drug form; and parenterally administering a pharmacologically acceptable amount of the suspension to the patient.

2. The method of claim 1, wherein the liposomes are about 0.2 microns in diameter.

3. The method of claim 1, wherein the liposome suspensions contain a lipophilic free radical quencher and a water-soluble iron chelator.

4. The method of claim 3 wherein the iron chelator is ferrioxamine.

5. The method of claim 3, wherein the lipid bilayer regions contains at least 0.1 mole percent of the lipophilic free radical quencher.

6. The method of claim 3, wherein the water-soluble iron chelator is a trihydroxamic acid.

7. A method of treating neoplasms in a human patient with at least the same extent of therapeutic effectiveness, but with substantially reduced incidence of alopecia and nausea with respect to that produced by treatment with doxorubicin in free form, comprising preparing, for parenteral administration, an aqueous suspension of liposomes (i) whose lipid bilayer region contains at least about 2.5 mole percent of doxorubicin or a pharmacologically acceptable salt thereof, and (ii) which are sized to allow for sterilization by filtration through a 0.45 micron pore size membrane, and which suspension contains less than about 20% doxorubicin in free-drug form; and parenterally administering a pharmacologically acceptable amount of the suspension to the patient.

8. A method of treating neoplasms in a human patient, comprising preparing, for parenteral administration, an aqueous suspension of liposomes (i) whose lipid bilayer region contains at least about 2.5 mole percent of an anthraquinone drug or a pharmacologically acceptable salt thereof, and (ii) which are sized to allow for sterilization by filtration through a 0.45 micron pore size membrane, and which suspension contains less than about 20% of the anthraquinone drug in free-drug form; and parenterally administering a pharmacologically acceptable amount of the suspension to the patient.

9. The method of claim 8, wherein the anthraquinone drug is selected from the groups consisting of doxorubicin, daunomycin, carcinomycin, N-acetyladriamycin, N-acetyldaunomycin, rubidazone, 5-imidodaunomycin, musettamycin, rudolfomycin, aclacinomycin, marcellomycin, descarbomethoxymarcellomycin, descarbomethoxyrudolfomycin, and mitoxanthrone.

* * * * *